US012765868B2

(12) United States Patent
Masotti et al.

(10) Patent No.: US 12,765,868 B2
(45) Date of Patent: Oct. 20, 2026

(54) DEVICE AND METHOD FOR THE TREATMENT OF CANCEROUS LESIONS AND THE LIKE

(71) Applicant: ELESTA S.P.A., Calenzano (IT)

(72) Inventors: Leonardo Masotti, Sesto Fiorentino (IT); Luca Breschi, Vaiano (IT); Tommaso Perretta, Calenzano (IT); Fabio Andreola, Calenzano (IT)

(73) Assignee: ELESTA S.P.A., Calenzano (IT)

( * ) Notice: Subject to any disclaimer, the term of this patent is extended or adjusted under 35 U.S.C. 154(b) by 1349 days.

(21) Appl. No.: 17/259,683

(22) PCT Filed: Jul. 8, 2019

(86) PCT No.: PCT/IB2019/055787
§ 371 (c)(1),
(2) Date: Jan. 12, 2021

(87) PCT Pub. No.: WO2020/012321
PCT Pub. Date: Jan. 16, 2020

(65) Prior Publication Data

US 2021/0128123 A1 May 6, 2021

(30) Foreign Application Priority Data

Jul. 13, 2018 (IT) ........................ 102018000007185

(51) Int. Cl.
*A61B 18/00* (2006.01)
*A61B 10/02* (2006.01)
(Continued)

(52) U.S. Cl.
CPC .......... *A61B 10/0275* (2013.01); *A61B 18/24* (2013.01); *A61B 2018/0022* (2013.01);
(Continued)

(58) Field of Classification Search
CPC ................ A61B 10/0275; A61B 18/24; A61B 2018/0022; A61B 2018/2005;
(Continued)

(56) References Cited

U.S. PATENT DOCUMENTS 5,599,295 A * 2/1997 Rosen .................... A61B 18/24
604/22
6,575,969 B1 6/2003 Rittman, III et al.
(Continued)

FOREIGN PATENT DOCUMENTS

CN 102179010 A 9/2011
WO 9304727 A1 3/1993

*Primary Examiner* — Tse Chen
*Assistant Examiner* — Martin Nathan Ortega
(74) *Attorney, Agent, or Firm* — McGlew and Tuttle, P.C.

(57) ABSTRACT

The device (1; 5) comprises: a protective cannula (7); a tubular suction member (9) coaxially housable in the protective cannula (7); a catheter (21), coaxially housable in the tubular suction member (9) and adapted to internally contain an optical fiber (23). The catheter is equipped, at a distal end (21 A) thereof, with an expandable balloon (25) adapted to be expanded by means of a fluid delivered through the catheter (21). The protective cannula (7) is axially movable with respect to the tubular suction member (9) and to the catheter (21).

11 Claims, 4 Drawing Sheets

(51) Int. Cl.
*A61B 18/24* (2006.01)
*A61B 18/20* (2006.01)

(52) U.S. Cl.
CPC ............... *A61B 2018/00333* (2013.01); *A61B 2018/00589* (2013.01); *A61B 2018/2005* (2013.01); *A61B 2218/002* (2013.01); *A61B 2218/007* (2013.01)

(58) Field of Classification Search
CPC ........ A61B 2218/001; A61B 2218/002; A61B 10/02; A61B 10/0233; A61B 10/0266; A61B 18/22; A61B 18/20; A61B 2218/00214; A61B 2218/00285; A61B 2218/2005
See application file for complete search history.

(56) References Cited

U.S. PATENT DOCUMENTS

| | | | | |
|---|---|---|---|---|
| 2004/0210278 | A1 | 10/2004 | Boll et al. | |
| 2005/0273145 | A1* | 12/2005 | Saab | A61F 7/123 607/113 |
| 2006/0253178 | A1* | 11/2006 | Masotti | A61N 5/0601 606/13 |
| 2017/0050043 | A1 | 2/2017 | Kang et al. | |
| 2019/0240505 | A1* | 8/2019 | Aljuri | A61B 8/085 |

* cited by examiner 1
3
3A
3B
5
7
7A
7B
9
9A
9B
11
11A
11B
13
15
17
19
21
21A
21B
21C
21D
21X
21Y
23
23A
24
25
27
29
31
Q
A
f7
II

DEVICE AND METHOD FOR THE TREATMENT OF CANCEROUS LESIONS AND THE LIKE

TECHNICAL FILED

The present invention relates to surgical devices for the treatment of cancerous lesions. Embodiments disclosed herein relate in particular to devices for minimally invasive treatment of breast lesions.

Methods for minimally invasive treatment of cancerous lesions, particularly breast lesions, are also disclosed.

BACKGROUND ART

Breast cancer is the leading cause of death from cancer in women and the first cause of death in different ages of life, representing 30% of the causes of oncological death before the age of 50, 22% between age 50 and 69 and 15% after age 70 (source ISTAT). A continuous trend towards a decrease in breast cancer mortality is observed (2.2%/year) which has been attributed to the greater diffusion of early diagnosis programs as well as to scientific progress with the evolution of therapeutic programs (Italian Association of Medical Oncology, 2017).

Increased attention to prevention has made it increasingly possible to diagnose early-stage breast cancer, particularly in the clinical stage Tla and Tlb, which include lesions of less than 1 cm without evidence of lymph node metastases. This allowed surgeons to perform increasingly conservative operation.

The evolution of treatment towards the use of minimally invasive techniques and operations, as well as a consequence of advances in diagnostic imaging, has now also become a necessity reinforced by the patients' increasingly urgent need for conservative operations.

A minimally invasive method such as thermoablation or laser thermotherapy has the advantage of obtaining a complete pathological response equal to surgical treatment, with a clear improvement in the aesthetic result, patient comfort and a reduction in morbidity and costs.

Laser light offers an excellent means of inducing a local increase in temperature in the tissue, which can be used for minimally invasive oncologic therapy through local temperature rise and subsequent induced tissue necrosis. Laser interstitial thermotherapy (LITT) is based on the positioning in the tumor tissue of one or more applicators capable of delivering a certain dose of laser energy for a certain time using very small optical fibers (diameter 0.3 mm). In percutaneous access, assisted by modern imaging techniques, introducer needles of different sizes are used for the positioning of optical fibers or laser energy applicators. After this initial step, the treatment starts with the switching on of the laser apparatus and the supply of energy. The radiation emitted by the applicator emitter diffuses into the surrounding tissues according to the laws of laser-tissue interaction.

Currently the diagnostic-therapeutic procedure involves the following sequence of operations:

A) vacuum-assisted lesion biopsy through multiple extraction of neoplastic tissue, for example through a bioptic technique performed with the Mammotome (registered trademark) or similar systems;

B) histological evaluation of biopsy frustules and tumor classification;

C) new surgical procedure to excise the lesion with a healthy margin;

D) post-surgical therapeutic treatments (determined by the result of the histological analysis).

The Bi-Rads classification, followed by histological confirmation of biopsy samples, gives rise to five possible results: B1-B2-B3-B4-B5 of which:

B1: normal tis sue

B2: benign lesion

B3: lesion with uncertain potential of malignancy; the overall positive predictive value of this category (VPP=number of malignant lesions found at surgery/surgical lesions) is about 25-35%.

B4: suspected lesion. The frequency of this diagnostic category is low in vacuum-assisted biopsy samples (<2%); the positive predictive value is 85%.

B5: malignant neoplastic lesion; it is a malignant lesion that can include carcinoma in situ, invasive carcinoma and other more rare malignancies (lymphomas, sarcomas, etc.).

The same Bi-Rads classification applies to micro-calcifications, for which histological confirmation is required as for tumor lesions. The method and the device described herein can also be used on micro-calcifications.

Currently, lesions classified as B4 and B5 are sent to surgery, the purpose whereof is to completely eradicate the disease by obtaining a healthy margin. B3 classified lesions require a more thorough evaluation, the result of which can lead to follow-up or subsequent exeresis surgery (more than 50% of cases).

B3 lesions inserted in the follow-up generally lead to a state of anxiety in the woman who lives with the possibility that the B3 lesion may increase in one of the subsequent controls and lead her towards a more radical surgical treatment. B3 lesions that are instead directed to surgery for high suspicion of malignancy are only 25-35% of malignant type and therefore determine an excess of therapy (exeresis surgery) in women in whom it would not have been necessary (65-75% cases). In any case, a part of women with B3 biopsy classification and all women with B4-B5 classification undergo, in addition to the vacuum-assisted biopsy procedure, a second surgical removal and enlargement of biopsy margins.

It would be desirable to identify new surgery techniques, and new instruments for this purpose, to reduce the drawbacks of the methods described above.

SUMMARY OF THE INVENTION

According to an aspect, a device is provided, comprising: a protective cannula; a tubular suction member coaxially housable in the protective cannula; a catheter, coaxially housable in the tubular suction member and adapted to internally contain an optical fiber; wherein the catheter is equipped, at a distal end thereof, with an expandable balloon adapted to be expanded by means of a fluid delivered through the catheter; and wherein the protective cannula is axially movable with respect to the tubular suction member and to the catheter.

Further advantageous features and embodiments of the device are described hereunder and are indicated in the appended claims, which form an integral part of the present description.

Also disclosed is a kit comprising a biopsy needle, for example but not exclusively a vacuum-assisted biopsy needle, with an external cannula and a device as defined above.

The device and the kit allow performing an operation of excision of tumor tissue from a lesion, or other, and performing a laser thermotherapy treatment of the margins of the cavity generated by the excision. It is thus possible to perform a minimally invasive procedure for treating the lesion by excision and subsequent coagulant treatment and/or clearing by laser radiation.

The action of coagulation and clearing has a dual purpose. First of all, the coagulation action is aimed at blocking any hemorrhage, both intra-procedural, which would lead to the premature interruption of the bioptic procedure, and post-procedural, which represents one of the most frequent complications with the need for subsequent therapeutic actions. The clearing action aims to destroy any tumor cells not extracted by the vacuum-assisted biopsy operation, or other core needle biopsies. For this last reason it is important to cause cell death in a portion of tissue surrounding the area subject to biopsy in order to obtain a safety margin around the tumor lesion.

The procedure may be particularly useful for the treatment of tumor lesions of the mammary gland, but the possibility is not excluded of applying the method and device disclosed herein to the treatment of other types of lesions, typically but not exclusively of tumor type, in humans and in animals, therefore both in the medical and veterinary field. The possibility of expanding the treatment to the plant sector is not excluded.

In some applications, the method may include a histological analysis in real time, i.e. extemporaneously, during the excision of the lesion tissues, so as to obtain a rapid and minimally invasive treatment, which can also reduce psychological as well as physical distress of the patient.

BRIEF DESCRIPTION OF THE DRAWINGS

The invention will be better understood by following the description and the accompanying drawings, which illustrate an exemplary and non-limiting embodiment of the invention. More particularly, the drawings show.

DETAILED DESCRIPTION OF EMBODIMENTS

Figures 1, 2:
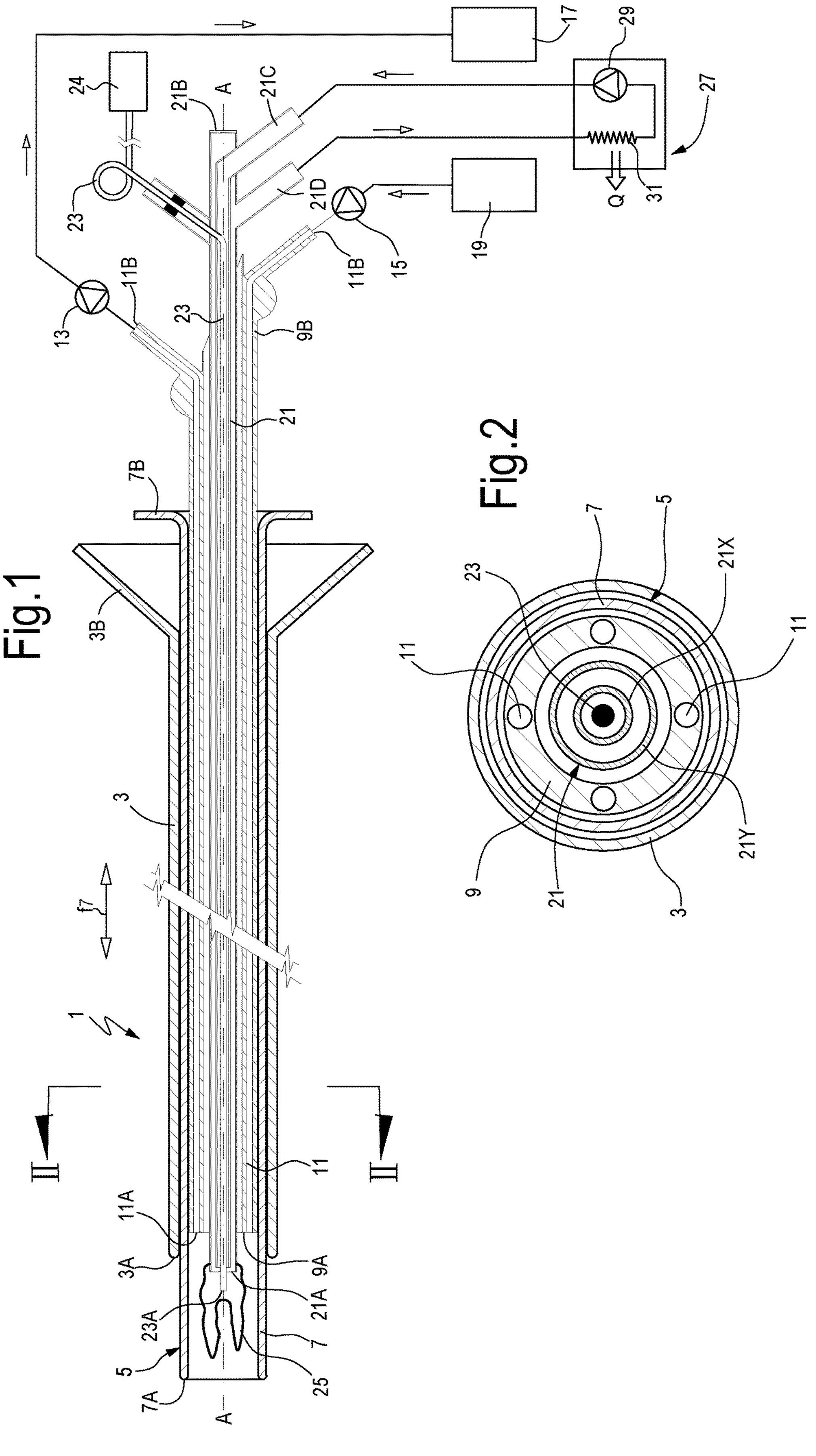
FIG. 1 a longitudinal section of a device for minimally invasive operations of neoplasms, especially, but not exclusively, of mammary neoplasms.
FIG. 2, a cross section according to line II-II of FIG. 1.
Figures 3A, 3B:
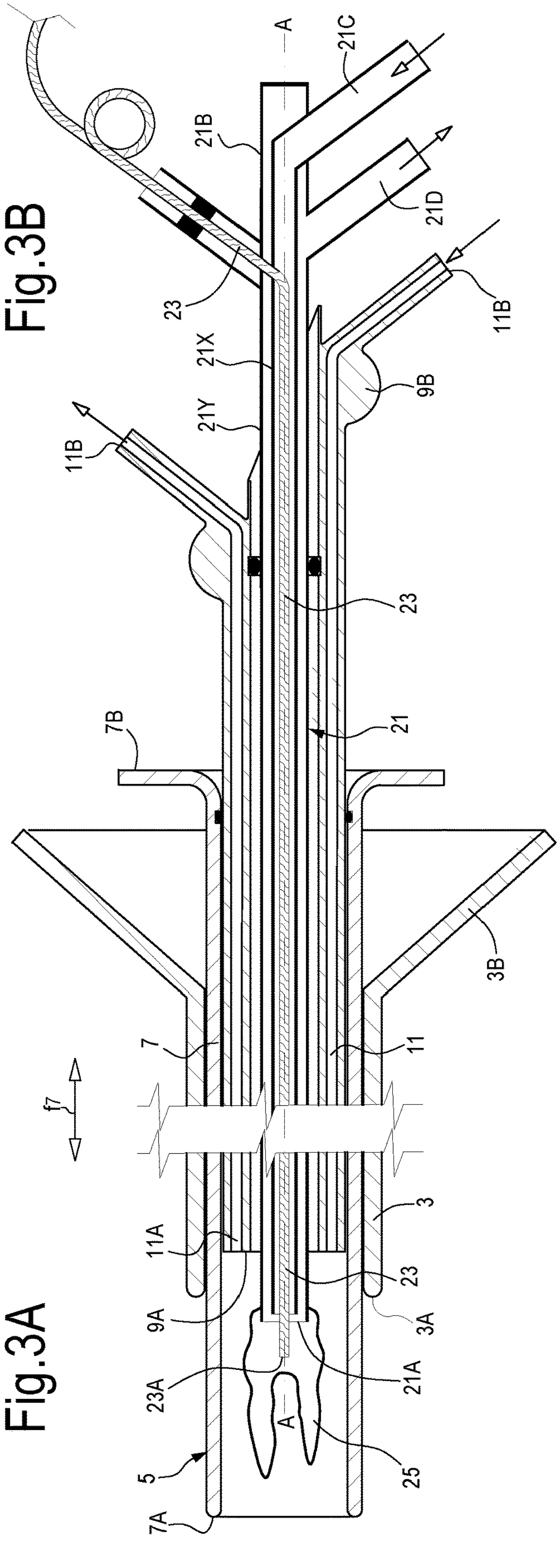
FIGS. 3A and 3B, enlargements of the distal portion and the proximal portion, respectively, of FIG. 1.

In embodiments described herein, the device can be combined with, or be part of, a kit for core needle biopsy of any type, for example for vacuum-assisted biopsies. The kit may also comprise an external cannula, which can be part of the device, or of the biopsy needle kit. The device is configured to perform a laser treatment of the margins of a cavity generated by the biopsy needle in the tissue being treated. The biopsy needle may be used to remove, in the form of one or more frustules of tissue, a cancerous lesion or the like, from an organ or tissue of a subject that requires treatment. Once the cavity has been generated in the tissue, and having removed the entire lesion tissue, it is possible to insert, preferably through the same cannula used for the removal of the lesion tissue through the biopsy needle, a device having a catheter adapted to contain an optical fiber and a dilatable or expandable balloon applied to or in the proximity of the distal end of the catheter.

The catheter may have one or two passages for introducing and removing a balloon expansion fluid. Preferably, two passages are provided to obtain a continuous or intermittent, i.e. discontinuous, circulation of expansion fluid. A tubular suction member may be associated with the catheter. This may be coaxial to the catheter and external thereto. In the wall of the tubular suction member one or more suction pipes may be formed and possibly one or more pipes for feeding a washing liquid, to wash the cavity before, after or during treatment.

With a kit of this type it is possible to perform a treatment method which provides for a first step of removal of the tissue of a lesion and a second step of laser treatment, clearing and/or coagulation, of the margins of the cavity generated by the removal. As will become apparent from the following description, the two treatment steps may be performed in the same session, in particular when the tissue extracted in the first step can be subjected to an extemporaneous, i.e. real time, histological analysis. This allows the introduction of a cannula through which the biopsy needle and subsequently the laser treatment device are then introduced in sequence, and without removal of the cannula.

In practice, the kit may comprise an external cannula, a biopsy needle and a laser treatment device. In other embodiments, the kit may comprise only the laser treatment device, which may be configured to work in combination with a biopsy needle kit, which may in turn comprise the external cannula.

The device for the clearing action by laser light may be used in combination with devices or kits for core needle biopsy of the Mammotome (registered trademark) type or others.

Coming now to the embodiment shown in the drawings, FIGS. 1, 2, 3A, 3B show a treatment device. The device is generally indicated with reference numeral 1. In the illustrated embodiment, the device 1 comprises, or is associated with, a main cannula or external cannula 3, which may be made, for example, of metal. The external cannula 3 may be part of a bioptic device, for example a device for performing vacuum-assisted biopsies. The cannula 3 may be used for example to insert a bioptic needle into the tissue or organ on which to perform a treatment. The external cannula 3 comprises a distal end 3A and a proximal end 3B.

By means of the external cannula 3 a laser treatment device can be inserted in the tissues to be treated, indicated below as composite organ 5, the various components whereof will be described in detail below. The composite member 5 is used to perform a laser thermotherapy treatment of a cavity made in the tissue to be treated by means of a bioptic needle or in another manner, preferably acting through the same external cannula 3 as described below with reference to an example of execution of a treatment procedure.

In some embodiments, the treatment device comprises the composite member 5 and the external cannula 3. In other embodiments, the external cannula 3 may be part of a biopsy kit, and the device in this case comprises the composite member 5 but not the external cannula 3. In some embodiments, the device may be part of a kit comprising: a bioptic needle, an external cannula 3 and a composite member 5.

The composite member 5 comprises a protective cannula 7 which, under conditions of use, is inserted inside the external cannula 3 approximately coaxially thereto. The protective cannula 7 has a distal end 7A and a proximal end 7B, on the operator's side. The protective cannula 7 is slidable according to the double arrow f7 inside the external cannula 3 for the purposes to be clarified below.

According to an exemplary embodiment, the protective cannula 7 houses a tubular suction member 9, substantially coaxial with the protective cannula 7 and having a cylindrical wall, a distal edge 9A and a proximal end 9B. The tubular suction member 9 is provided with one or more pipes 10 11, made in the thickness of the cylindrical wall of the tubular suction member 9. Preferably, the pipes 11 are in even number. Preferably, the pipes 11 are equidistant from each other, i.e. they are arranged with a constant angular pitch around the axis A-A of the tubular suction member. The pipes 11 may also be made differently, for example as thin tubes arranged around the axis of the protective cannula 7 and therein. However, 15 making the pipes 11 in the thickness of part of a tubular member 9 is particularly advantageous, for example in terms of constructive simplicity.

In advantageous embodiments, the pipes 11 have anti-clogging features.

In the illustrated example, the pipes 11 have distal ends 11A (FIG. 3A) aligned on the distal edge 9A of the tubular suction member 9. In other embodiments, not shown, the pipes 11 may have distal ends distributed in various positions, both on the distal edge 9A, and retracted with respect thereto, on the outer surface of the tubular suction member 9. Each pipe 11 may extend from the respective distal end 11A to a proximal end 11B, i.e. an end facing the operator. The proximal end 11B of at least one of the pipes 11 may be placed in fluid communication with a suction member schematically indicated with reference numeral 13 (FIG. 1). In some embodiments, all the pipes 11 may be placed in fluid communication with a suction member or with several suction members 13.

In other embodiments, the proximal end 11B of at least one of the pipes 11 may be placed in fluid communication with a fluid feed member 15. Preferably, at least one of the pipes 11 may be connected to a suction member 13 and at least another of the pipes 11 may be connected to a fluid feed member 15, so as to generate a circulation of fluid as described in greater detail below and for the purposes clarified below.

The suction member may be fluidly coupled to a collection tank 17, while the feed member 15 may be fluidly coupled to a dispensing tank 19 of a washing liquid, for example a physiological solution.

Coaxially to the tubular suction member 9 and in the interior thereof there is a catheter 21, which houses an optical fiber 23, extending approximately coaxially to the catheter 21. The optical fiber 23 may be connected to a laser source 24.

The distal end 21A of the catheter 21 may be associated with an expandable balloon 25. In particular, in some embodiments the expandable balloon 25 may be fixed to the distal end 21A of the catheter 21 with a sealed connection, so that the balloon 25 can be dilated by introducing a fluid through the catheter 21, as described in more detail below. The distal end 23A of the optical fiber 23 may protrude from the distal end 21A of the catheter 21 and lead into the expandable balloon 25. In some embodiments, the optical fiber 23 may be slidable in the catheter 21 to make the distal end or tip 23A thereof protrude more or less from the catheter 21 towards the inside of the expandable balloon 25.

The proximal end 21B of the catheter 21 may be connected to a feed circuit of a filling and expansion fluid of the expandable balloon 25. In a possible embodiment, the proximal end 21B of the catheter 21 may have an inlet connection 21C for a fluid, typically a biocompatible liquid. The biocompatible fluid may be fed by a pumping system and may come from a feeding tank. The same connection 21C may also be used to remove the filling and expansion fluid of the expandable balloon 25 at the end of the treatment, so that the expandable balloon 25 may return to its minimum volume and be extracted from the organ being treated.

In other embodiments, as illustrated in the drawing, a continuous or discontinuous circulation of the filling and expansion fluid of the expandable balloon 25 may be provided. For this purpose it may be provided, as shown in the figures, that the catheter 21 has an external tubular element 21*y* and an internal tubular element 21*x* (see in particular FIGS. 2, 3A, 3B) substantially coaxial to each other, which define an annular conduit therebetween. The optical fiber 23 is housed in the internal tubular element 21*x*. In this way, the catheter 21 has two passages for the introduction of the filling and expansion fluid into the expandable balloon 25 and the extraction of the filling and expansion fluid from the expandable balloon 25. For example, the filling and expansion fluid may be fed into the expandable balloon 25 through the connection 21C and the annular passage between the optical fiber 23 and the internal tubular element 21*x*, and may be removed from the expandable balloon 25 through the annular passage between the internal tubular element 21*x* and the external tubular element 21*y* and through an outlet connection 21D.

The inlet and outlet connections 21C, 21D are adapted to connect the catheter 21 and therefore the expandable balloon 25 to an expansion circuit, schematically indicated with 27, in which a filling and expansion fluid of the expandable balloon 25 circulates. Schematically, the expansion circuit 27 comprises a circulation pump 29 and may comprise a heat exchanger 31, to extract heat Q from the filling and expansion fluid circulating in the circuit.

The expansion circuit 27 is adapted to circulate the filling and expansion fluid of the expandable balloon 25, so as to maintain a sufficient pressure in the expandable balloon 25, capable of causing it to expand to the desired size, and at the same time extracting heat from the tissues treated by the circulating fluid.

In other embodiments, not shown, the catheter 21 may be provided with a single connection 21C to a circuit for feeding a filling and expansion fluid of the expandable balloon 25. In this case, the fluid is introduced into the expandable balloon 25 to expand it, but it is not circulated. At the end of the treatment, the fluid is discharged from the expandable balloon 25 through the same connection through which said fluid was introduced into the expandable balloon to inflate it. In this case, the external tubular element 21*y* and the outlet connection 21D may be omitted to the advantage of a smaller diameter of the catheter 21.

In some embodiments, the filling and expansion fluid supplied in the expandable balloon 25 may comprise diffusing particles, for example particles of hydroxyapatite, $TiO_2$, $TiO_2$, $Al_2O_3$, $BaSO_4$, to obtain a more uniform diffusion of the laser radiation emitted from the tip of the optical fiber 23. The use of diffusing particles may be particularly useful in case the optical fiber 23 has a flat tip 23A. In other embodiments, other features may be envisaged to obtain an approximately spherical distribution of the optical radiation coming from the optical fiber 23, for example an optical fiber 23 with a conical tip may be used.

Having described the device 1, the steps of a possible treatment method will now be illustrated. By way of example, reference is made to a procedure for the treatment of a lesion in a mammary gland M. The possibility of using the device and the method described herein for the treatment of other types of lesions, in particular other neoplastic lesions, is not excluded.

The steps of the procedure are schematically illustrated in the sequence of FIGS. 4A to 4F.

In a possible embodiment, the treatment process may provide a first step of excision of the tumor lesion by means of a vacuum-assisted biopsy system or another system typically employing a biopsy needle.

The excision step may take place through multiple extraction of neoplastic tissue with a vacuum-assisted system, for example with a Mammotome system (registered trademark). More generally, excision may take place via a minimally invasive device introduced into the tissue of the mammary gland (or other organ to be treated) through a cannula, such as the external cannula 3 described above.

Figure 4A:
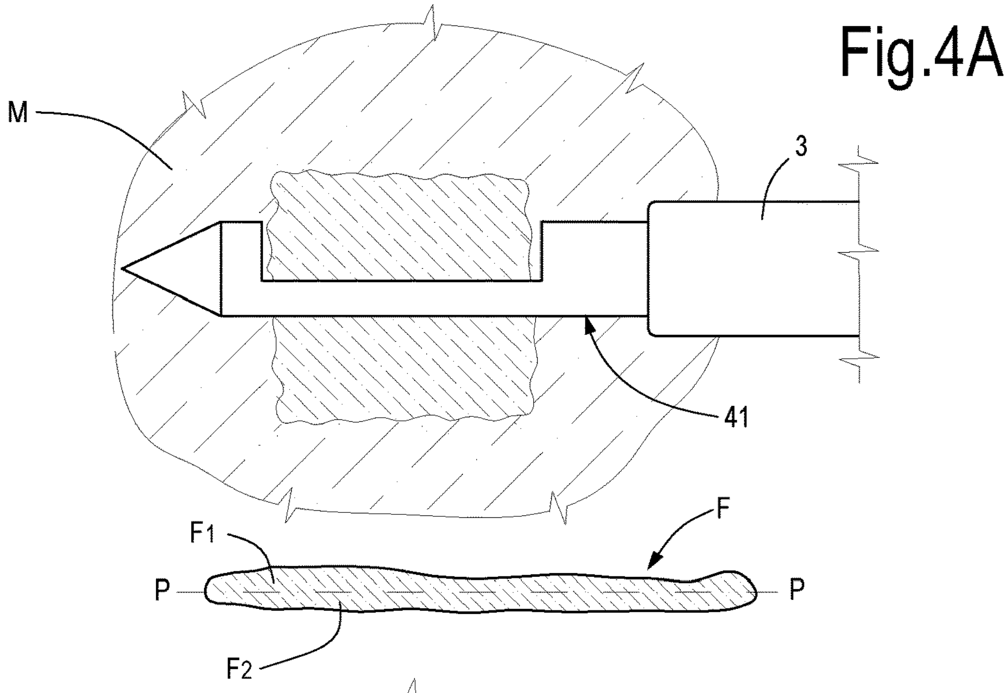
FIGS. 4A-4F, a sequence of steps of an operation that can be carried out with the device of FIGS. 1 to 3.
Figure 4B:
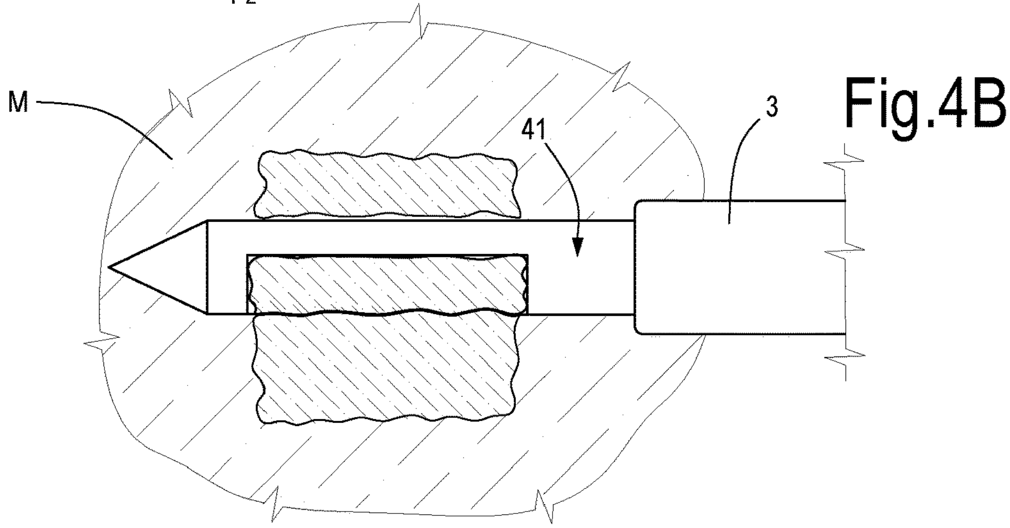

FIGS. 4A, 4B show this treatment step. A bioptic suction needle, i.e. a needle for vacuum-assisted biopsy, indicated with 41, or another suitable surgical instrument, is introduced into the tissues where the tumor lesion T to be removed is located. The introduction may take place via the external cannula 3. The excision procedure may be performed under the control of an ultrasound device or other imaging system.

In the procedure described herein, the removal of tissue frustules may be repeated several times until all the suspicious tissue is removed, leaving an empty cavity CV in the tissues.

Figure 4C:
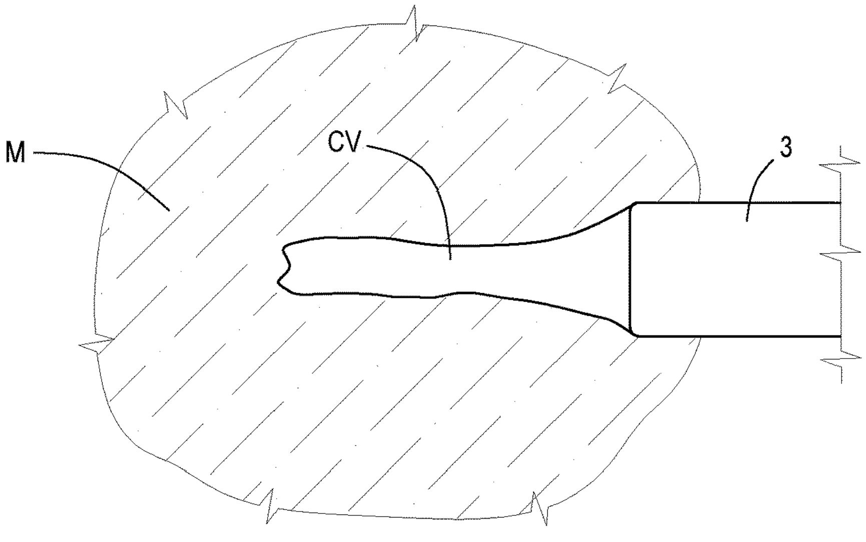

This peculiarity can be understood from the sequence of FIGS. 4A, 4B, 4C. FIGS. 4A, 4B show two successive maneuvers (not necessarily sequential, since other operations can be performed with a different angular position of the needle 41), with which two frustules of tissue are removed. At the end of this first part of the procedure, reserved for the excision of the mass (FIG. 4C), the bioptic needle 41 can be removed through the external cannula 3, which can remain inserted in the tissue. In front of the distal end of the external cannula 3 a cavity CV remains, previously occupied by the removed tissue. In FIG. 4C, the cavity CV is shown as an empty space, although this space may actually be temporarily occupied, wholly or in part, by the surrounding tissue which fills, until the subsequent operation described below, the space previously occupied by the tissue excised by the bioptic needle 41.

Each extracted frustule, or at least some of them, can be subjected to a real time, i.e. extemporaneous, histological analysis. For real-time or extemporaneous analysis it is meant in this context a histological analysis that is performed during the surgical session. The extemporaneous histological analysis allows the operator to decide if and to what extent execute tissue excision operations, to eliminate the entire tumor mass, with subsequent maneuvers through the bioptic needle (or other suitable instrument) through the external cannula 3.

During the first steps of the operation, in some embodiments, it may be envisaged to divide each frustule or sample of extracted tissue (or at least some of them) into two portions, for example according to a longitudinal plane, in order to obtain a first portion of the tissue sample, which is subjected to real-time histology analysis, and a second portion of the same frustule, or tissue sample, which is used for a second delayed histological analysis, for prognostic factors and associated post-treatment therapy. FIG. 4A schematically shows a frustule F which is divided along a longitudinal plane PP in two portions F1, F2. One of the two portions F1, F2 is used for extemporaneous histological analysis and the other is preserved for subsequent histological analysis.

As indicated above, the collection of samples is repeated several times until complete excision of the tumor tissue, allowed by the bioptic needle. The execution of real time histological analysis allows immediately verifying the nature of the lesion. In practice, the next step is performed if and only if the histological analysis ascertains that the removed tissue falls within a lesion classified as B3 or B4 or B5 as defined above.

If the real time histological analysis ascertains that the lesion is malignant or potentially malignant, the next step of clearing, and possibly coagulation, is carried out, preferably during the same session, by laser hyperthermia of the lesion margin, i.e. of the residual cavity surface CV. Advantageously, this second step is preferably carried out using the same external cannula 3, used to introduce the bioptic needle, to insert the laser treatment member 5.

In the second step, the bioptic needle 41 is first extracted from the external cannula 3. Subsequently, the device 5 is introduced through the same external cannula 3, and more precisely the components inside the external cannula 3 which is already in place.

Figure 4D:
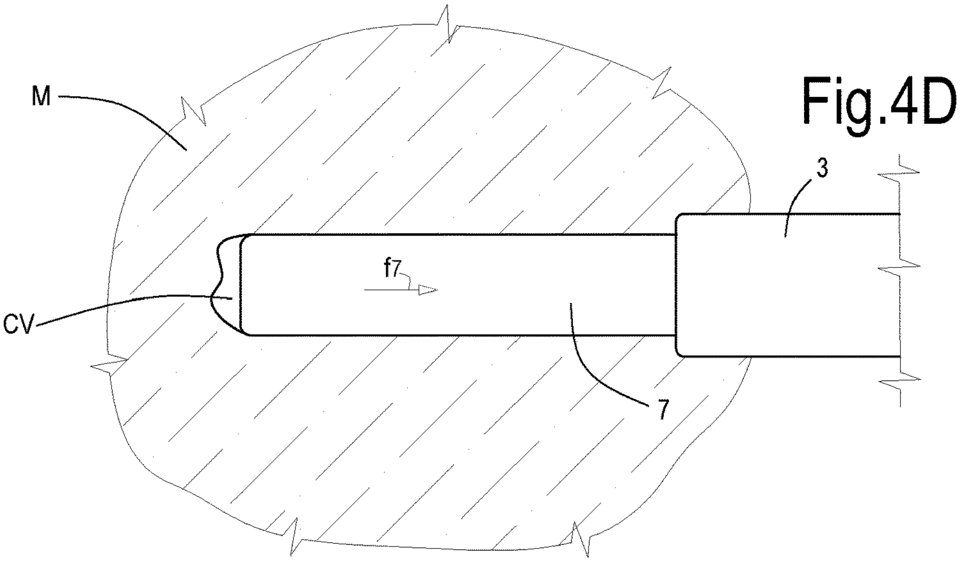

Such an introduction, schematically represented in FIG. 4D, can be performed under the control of an ultrasound or other imaging device. The composite member 5 is used in the arrangement of FIGS. 1, 3A, 3B, that is with the expandable balloon 25 deflated and protected inside the protective cannula 7.

Figure 4E:
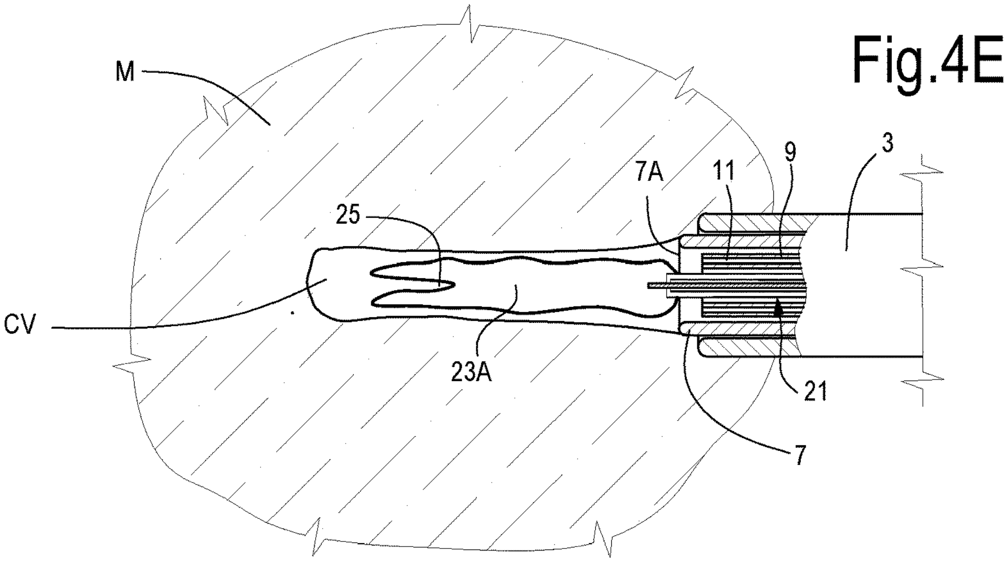

Once the distal portion 7A of the protective cannula 7 of the composite organ 5 has been brought into the cavity CV formed in the tissue of the mammary gland M in the previous stage of removal by the bioptic needle 41 of the tumor mass, the protective cannula 7 can be retracted inside the external cannula 3, keeping the catheter 21 and the expandable balloon 25 axially stationary, so that the protective cannula 7 releases the expandable balloon 25 in the cavity CV. This step is schematically illustrated in FIG. 4E.

Figure 4F:
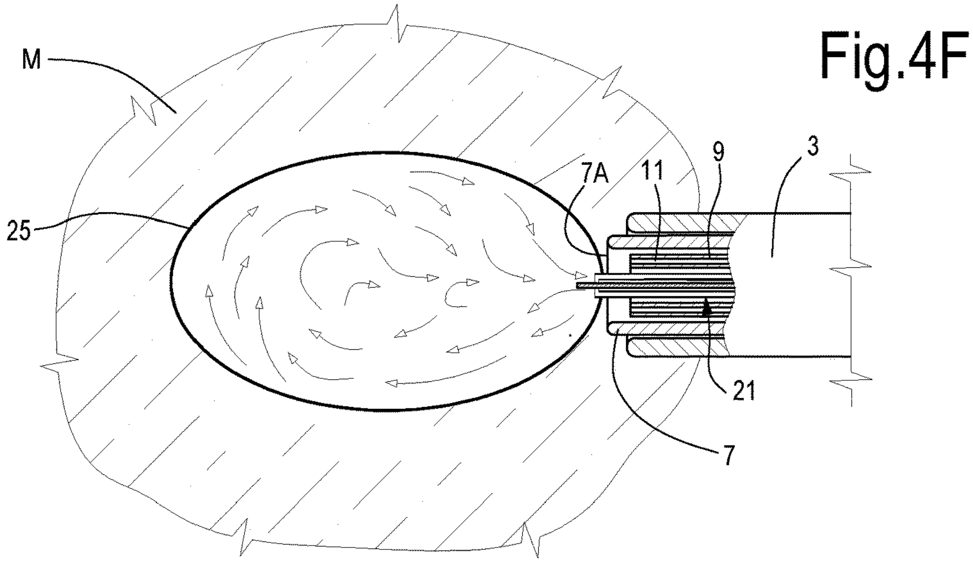

Having reached this condition, the expandable balloon 25 which is located in the cavity CV can be expanded by the filling and expansion fluid coming from the expansion circuit 27. The pressure of the filling and expansion fluid is such as to make the expandable balloon 25 adhere to the internal surface of the cavity CV, compressing the surrounding tissues. FIG. 4F shows the situation reached at the end of the expansion step of the expandable balloon 25.

The filling and expansion fluid can be fed until a suitable pressure and thus a suitable expansion of the expandable balloon 25 are reached and then the feeding of fluid can be interrupted, maintaining the pressure inside the expandable balloon 25 at the pressure reached. On the other hand, in other embodiments the filling and expansion fluid can be made to circulate continuously or discontinuously in the expandable balloon 25, for example to remove heat from the treated area, avoiding localized overheating and any phenomena of tissue carbonization, which could slow down or hinder the spreading of the laser radiation.

Once the balloon 25 has reached the expanded condition, as in FIG. 4F, the clearing step of the margins of the removed lesion can be carried out, i.e. the step of clearing the surface of the tissues that delimits the cavity CV that was created in the previous excision step. For this purpose, laser radiation is injected into the optical fiber 23 by the laser source 24 and radiated through the tip, or distal end 23A, of the optical fiber 23 into the internal volume of the expandable balloon 25. The radiation, directly or after multiple reflections and diffusions through diffusing particles contained in the filling and expansion liquid, passes through the wall of the expandable balloon 25, which is for this purpose transparent or diffusing at the wavelength of the laser radiation. The radiation emitted through the wall of the expandable balloon 25 affects the surrounding tissues.

The heat generated by the absorption of laser radiation in the tissues surrounding the cavity CV causes denaturation and therefore clearing of the tissues surrounding the cavity CV, creating a sufficient safety margin, with the elimination of any residual tumor cells. Furthermore, the thermal energy has a coagulation effect, which avoids, reduces or stops the possible bleeding that can be caused by the previous operation of excision of the tumor tissue.

During one or more of the steps described above, by means of the tubular suction member 9 it is possible to activate a suction through at least one, some or all the pipes 11, for example to remove debris, in liquid, solid or gaseous form, generated in the cavity CV during laser treatment. In the embodiment of FIGS. 1, 2, 3A, 3B the pipes 11 all end in the same axial position, which advantageously lies (when the device is in the operative position) behind the tip of the optical fiber 23, i.e. in a position set back with respect to the distal end 23A of the optical fiber 23, so as not to interfere with the delivery of laser energy. As mentioned, however, the possibility that the pipes 11 have different lengths, and for example have a variable extension beyond the distal end of the tubular member 9 is not excluded.

While in some embodiments all the pipes 11 can be suction pipes, in other embodiments, as schematically indicated in FIG. 1 and described above, at least one of the pipes 11 is a suction pipe and at least one of them is configured to deliver a washing fluid, so as to perform a continuous or intermittent washing of the cavity CV during one or more of the steps of the procedure described herein, and typically during the laser energy delivery step.

Once the laser treatment step is over, the instrument can be extracted and the patient can undergo, in the usual times and ways, post-surgical therapeutic treatments, which are determined by the result of the deferred histological analysis performed on the samples that were not used for real time histological analysis. Histological analysis can also be performed on any new biological samples surgically taken from the mammary gland tissue, surrounding the laser cleared portion. This is appropriate, in particular in the step of verification and development of the method described herein.

To extract the instrument, a sequence of operations can be performed that is inverse with respect to the one described above. Firstly, once the delivery of laser radiation by the source 24 has been interrupted, the expandable balloon 25 is collapsed by drawing from it the fluid with which it was previously expanded. Once the expandable balloon 25 has contracted, the distal portion 7A of the protective cannula 7 is advanced until the entire expandable balloon 25 is protected therein. The composite member 5 comprising the protective cannula 7, the tubular suction member 9, the catheter 21, the optical fiber 23 and the expandable balloon 25 is then extracted by sliding inside the external cannula 3. Finally, the external cannula 3 is removed.

On the other hand, the catheter 21 can be retracted with the expandable balloon 25 adhered thereto in the protective cannula 7 and subsequently the protective cannula 7 can be retracted from the external cannula 3. In other embodiments, the retraction movements of the catheter 21 and expandable balloon 25, protective cannula 7 and external cannula 3 can be performed in any other appropriate sequence, which avoids the risk of damaging the tissues and/or components of the device.

As will be understood from the above description, in this way a minimally invasive method is obtained with which a cavity CV is formed within the organ M to be treated, and inside which, in the context of the same operation session, laser energy is subsequently dispensed to clear for therapeutic purposes a suitable tissue thickness, for example from about 0.1 mm to about 20 mm, preferably from about 1 mm to about 10 mm—blocking at the same time by coagulation any hemorrhages originated from the walls of the cavity or in ducts or vessels inside biological tissues treated.

The proposed method does not alter the post-surgical therapeutic path in any way (for example pharmacological therapies deemed necessary by the oncologist).

In the description of the treatment method illustrated in FIGS. 4A-4F it has been hypothesized to perform an extemporaneous histology analysis, on the basis of the outcome whereof subsequent operations are performed for further excision and laser thermotherapy treatment. However, the method and the device described herein also apply to the treatment of lesions for which, for whatever reason, it is not possible to proceed with an extemporaneous histological analysis. This occurs, for example, for some types of suspected micro-calcifications that require histological confirmation. In this case, a biopsy is initially performed in a first operation session. This is followed by a histological analysis in the laboratory.

The biopsy can be performed with a bioptic needle for vacuum-assisted biopsy, or with another type of instrument, advantageously through the protective cannula 3 substantially as described above and illustrated in FIGS. 4A-4C, until a cavity CV is obtained in the tissues. The excision step can be carried out until the lesion has been completely removed.

The removed tissues are subsequently subjected to histological analysis in the laboratory. On the basis of the results of the tests, the second step of the treatment can be performed, consisting in the laser clearing thermotherapy of the lesion margins. In this case, since the histological analysis is performed after the biopsy, the second step of the operation is performed in a second session, again introducing an external cannula 3 until it reaches the cavity previously formed and then introducing through the external cannula 3 the composite member 5 and carrying out the above described operations illustrated in FIGS. 4D, 4E, 4F.

The possibility of implementing the method with histological analysis delayed in a different manner is not excluded, performing a first removal of tissues in the first step, followed by histological analysis. If the histological analysis confirms the need for total excision and laser treatment, in the second step, the excision of the lesion mass can be completed and then the laser treatment is performed. In this case, in essence the removal of the tissue is carried out partly in the first step (first session of operation) and partly in the second step (second session of operation).

Ultimately, the mini-invasiveness of the procedure allows an easy application of the method both at the same time as the biopsy procedure, i.e. by performing the biopsy in real time or extemporaneously, and in the case in which the histological analysis is performed in the laboratory on samples taken in a first operation session and the laser treatment is delayed to a second session.

The expandable balloon 25 may have variable shapes, which can be selected depending on the shape of the cavity CV that is formed in the tissue to be treated. In some embodiments, the expandable balloon may have, in an inflated configuration, a spherical or spherical-like shape, i.e. an elliptical section with a minor axis and a major axis which are in a ratio close to 1, typically greater than about 0.7, for example greater than about 0.8. In other embodiments, the expandable balloon 25 may have, in an inflated configuration, a cylindrical, or dog bone shape, or any other suitable shape. The expandable balloon 25 can be made of a flexible and substantially inextensible material, or it can be made of an extensible material, for example capable of extending elastically or plastically when subjected to a suitable internal pressure. Although particular reference has been made in the foregoing description to the use of the method and the device described herein for the treatment of tumor lesions of the mammary gland, it should be understood that at least some of the advantages of the device and of the method of the present disclosure can also be used in the treatment of other lesions, especially of tumor-type, i.e. neoplastic, of different organs, preferably soft tissue such as, but not limited to, liver, thyroid, prostate, kidney or other soft tissue. Moreover, the technology, the methods and the devices disclosed herein can be applied not only in medicine, but also in veterinary medicine, for the treatment of similar diseases in animals. The possibility of using the methods and devices illustrated in applications in the plant world is not excluded.

Moreover, although specific application examples have been illustrated with reference to the use of vacuum-assisted biopsy needles, i.e. in which tissue excision is facilitated or promoted through the use of suction, it must be understood that in order to remove the lesion, for example the tumor tissue, different instruments can be used, and in particular biopsy needles based on different working principles. In embodiments described herein, therefore, the bioptic needle may be any tissue excision device, in particular insertable into an organ or other site in which the lesion to be treated is located, for example through an external cannula.

In this regard, it should be noted that the external cannula, such as for example the cannula 3 described with reference to the accompanying figures, may have any shape suitable for working with a specific bioptic needle, or imposed by the type of bioptic needle used. For example, in the case of a bioptic needle for vacuum-assisted biopsy, such as a Mammotome (registered trademark), the cannula 3 may have a noncircular cross-section. The protective cannula 7 and/or other components of the composite member 5 may be shaped so as to have a cross-section compatible with the cross-section of the cannula 3 of the bioptic needle or used in combination with the bioptic needle.

The present disclosure specifically concerns a method as defined in the following clauses:

Clause 1. A method for treating a lesion in a tissue, comprising the following steps:

- inserting in the tissue an external cannula (3) up to adjacent to a cavity (CV) obtained in the tissue by excision of tissue of said lesion;
- inserting a laser thermotherapy treatment device (1; 5) through an external cannula (3) towards said cavity (CV);
- delivering laser energy into said cavity (CV) through an optical fiber (23) of the device (1).

Clause 2. A method for treating a lesion in a tissue, comprising the following steps:

- inserting an external cannula (3) into the tissue;
- inserting a bioptic needle (41) towards the lesion (T) through the external cannula (3);
- removing, through the bioptic needle (41), at least one frustule (F) of tissue from the lesion (T), and preferably removing the maximum part of the lesion, to the extent allowed by the bioptic needle, generating a cavity (CV) in the tissue;
- extracting the bioptic needle (41) from the external cannula (3);
- inserting a laser thermotherapy treatment device (1; 5) towards the cavity (CV) obtained by extracting said at least one tissue frustule;
- delivering laser energy into said cavity (CV) through an optical fiber (23) of the device (1) and clearing the margin of the lesion through said laser energy.

Clause 3. The method of clause 2, wherein the step of inserting the laser thermotherapy treatment device towards said cavity comprises the steps of:

- after extraction of the biopsy needle from the external cannula (3), keeping the external cannula in place;
- inserting the laser thermotherapy treatment device through the same cannula kept in place until it reaches the cavity obtained through the bioptic needle.

Clause 4. The method of clause 2 or 3, wherein the step of removing at least one frustule (F) of tissue from the lesion comprises the step of sequentially removing a plurality of frustules, until complete removal of the lesion.

Clause 5. The method of clause 2 or 3 or 4, further comprising the step of performing, on said at least one frustule a real time, i.e. extemporaneous, histological analysis.

Clause 6. The method of clause 5, comprising the step of dividing said at least one frustule into at least two portions, preferably along a separation plane parallel to a longitudinal development of said frustule.

Clause 7. The method of clause 6, comprising the steps of:

a. performing the real time histological analysis on a first one of said at least two portions;

b. keeping a second one of said at least two portions for a deferred histological analysis.

Clause 8. The method of one or more of the preceding clauses, wherein the step of removing at least one tissue frustule (F) comprises the steps of sequentially removing a plurality of tissue frustules (F) through said bioptic needle (41), at least some of said frustules (F) being subjected to real time histological analysis.

Clause 9. The method of clause 8, wherein the step of sequentially removing a plurality of tissue frustules (F) through said bioptic needle (41) comprises the steps of positioning the bioptic needle in a plurality of sequential angular positions mutually offset around an axis of the bioptic needle; in each of said angularly offset positions collecting a tissue frustule.

Clause 10. The method of one or more of clauses 2 to 9, wherein the bioptic needle (41) is a bioptic needle for vacuum-assisted biopsy.

Clause 11. The method of one or more of the preceding clauses, wherein the step of dispensing laser energy in said cavity (CV) comprises the step of removing liquid, solid or gaseous debris by suction from the cavity through a suction pipe, for example adjacent to the catheter which contains the optical fiber (23) or coaxial thereto.

Clause 12. The method of clause 11, wherein the step of removing debris by suction from the cavity includes the step of dispensing a washing liquid into the cavity and suctioning the washing liquid and the debris from the cavity.

Clause 13. The method of one or more of the preceding clauses, wherein the step of dispensing laser energy in the cavity (CV) comprises the steps of:

- inserting in the cavity an expandable balloon (25) in which the optical fiber (23) leads;
- expanding the expandable balloon (25) in the cavity (CV) by means of a filling and expansion fluid, so as to stretch the cavity (CV) walls;

delivering laser energy through the expanded volume of the expandable balloon (25) and through a flexible wall of said balloon, adhering to the cavity walls.

Clause 14. The method of clause 13, wherein the expansion fluid contains diffusing particles to diffuse laser energy delivered by a fiber tip in a uniform manner towards the wall of the expandable balloon (25).

Clause 15. The method of clause 13 or 14, further comprising the step of continuously or discontinuously circulating the expansion fluid in the expandable balloon (25).

Clause 16. The method of one or more of the preceding clauses, wherein the step of inserting the device (1; 5) towards the cavity (CV) comprises the steps of:

inserting in the external cannula (3) a protective cannula (7), containing a catheter (21) therein with an expandable balloon (25) at its distal end (21A); the catheter (21) containing the optical fiber (23); the distal end (21A) of the catheter (21) and the expandable balloon (25) being integrally contained within the protective cannula (7);

bringing the end of the protection cannula (7), and the expandable balloon (25) contained therein, beyond a distal end (3A) of the external cannula (3) into the cavity (CV);

retracting the protective cannula (7) inside the external cannula (3) towards a proximal end (3B) of the external cannula (3);

expanding the expandable balloon (25) into the cavity (CV);

delivering laser energy by means of the optical fiber (23) through the expanded balloon (25).

Clause 17. The method of clause 16, further comprising the steps of:

inserting into the external cannula (3) a tubular suction member (9) housed in the protective cannula (7);

during the step of dispensing laser energy through the optical fiber (23), generating suction in said cavity (CV) through the tubular suction member (9).

Clause 18. The method of clause 17, further comprising the steps of:

inserting into the external cannula (3) a tubular suction member (9) housed in the protective cannula (7), said tubular suction member (9) being provided with suction pipes, said pipes preferably having anti-clogging features, and with washing liquid feeding pipes; the catheter (21) being disposed in the tubular suction member (9);

during the laser energy supply step through the optical fiber (23), by means of the feeding pipes feeding into said cavity a washing liquid and suctioning the washing liquid and debris from the cavity through the suction pipes.

The invention claimed is:

1. A device for the treatment of cancerous lesions the device comprising:

a protective cannula;

a tubular suction member adapted to be coaxially housed in the protective cannula, the tubular suction member comprising a cylindrical wall and a distal edge; and a catheter, adapted to be coaxially housed in the tubular suction member and adapted to internally contain an optical fiber;

wherein at a distal end of the catheter an expandable balloon is fixed with a sealed connection, so that the expandable balloon can be expanded by means of a fluid delivered through the catheter, the catheter being adapted to project from the distal edge of the tubular suction member with the expandable balloon outside the tubular suction member;

the optical fiber and the expandable balloon being configured to emit optical energy from a distal end of the optical fiber into the expandable balloon and through a balloon wall when the expandable balloon is expanded;

wherein the protective cannula is axially movable with respect to the tubular suction member and to the catheter;

wherein at least one suction pipe and at least one washing liquid feed pipe are provided in the cylindrical wall of the tubular suction member;

wherein said at least one suction pipe and said at least one washing liquid feed pipe each has a distal end at the distal edge of the cylindrical wall; and wherein the catheter has two passages, respectively for the entry and for the exit of a fluid for filling and expanding the expandable balloon.

2. The device of claim 1, wherein the catheter comprises an external tubular element and an internal tubular element coaxial to each other, which define an annular conduit therebetween; wherein the optical fiber is housed in the internal tubular element; and wherein the expandable balloon is fixed to a distal end of the external tubular element with said sealed connection.

3. The device of claim 1, further comprising an external cannula adapted to slidably receive the protective cannula.

4. The device of claim 1, wherein a plurality of suction pipes are provided in the thickness of the tubular suction member.

5. The device of claim 1, wherein a plurality of washing liquid feed pipes are provided in the thickness of the tubular suction member.

6. The device of claim 1, wherein each suction pipe is connectable to a suction line and each washing liquid feed pipe is connectable to a washing liquid feed line.

7. The device of claim 1, wherein said at least one suction pipe and said at least one washing liquid feed pipe have a distal end on the distal edge of the tubular suction member.

8. A kit for the treatment of cancerous lesions, the kit comprising:

a device for the treatment of cancerous lesions, the device comprising: a protective cannula; a tubular suction member adapted to be coaxially housed in the protective cannula, the tubular suction member comprising a cylindrical wall and a distal edge; a catheter, adapted to be coaxially housed in the tubular suction member and adapted to internally contain an optical fiber; wherein at a distal end of the catheter an expandable balloon is fixed with a sealed connection, so that the expandable balloon can be expanded by means of a fluid delivered through the catheter, the catheter being adapted to project from the distal edge of the tubular suction member with the expandable balloon outside the tubular suction member; the optical fiber and the expandable balloon being configured to emit optical energy from a distal end of the optical fiber into the expandable balloon and through a balloon wall when the expandable balloon is expanded; wherein the protective cannula is axially movable with respect to the tubular suction member and to the catheter; wherein at least one suction pipe and at least one washing liquid feed pipe are provided in the cylindrical wall of the tubular suction member; wherein said at least one suction pipe and said at least one washing liquid feed pipe each has a distal end at the distal edge of the cylindrical wall;

wherein the catheter has two passages, respectively for the entry and for the exit of a fluid for filling and expanding the expandable balloon;

an external cannula adapted to slidably receive the protective cannula; and a bioptic needle insertable in the external cannula.

9. A medical apparatus comprising a device for the treatment of cancerous lesions, comprising: a protective cannula; a tubular suction member adapted to be coaxially housed in the protective cannula, the tubular suction member comprising a cylindrical wall and a distal edge; a catheter, adapted to be coaxially housed in the tubular suction member and adapted to internally contain an optical fiber; wherein at a distal end of the catheter an expandable balloon is fixed with a sealed connection, so that the expandable balloon can be expanded by means of a fluid delivered through the catheter, the catheter being adapted to project from the distal edge of the tubular suction member with the expandable balloon outside the tubular suction member; the optical fiber and the expandable balloon being configured to emit optical energy from a distal end of the optical fiber into the expandable balloon and through a balloon wall when the expandable balloon is expanded; wherein the protective cannula is axially movable with respect to the tubular suction member and to the catheter; wherein at least one suction pipe and at least one washing liquid feed pipe are provided in the cylindrical wall of the tubular suction member;

wherein said at least one suction pipe and said at least one washing liquid feed pipe each has a distal end at the distal edge of the cylindrical wall; wherein the catheter has two passages, respectively for the entry and for the exit of a fluid for filling and expanding the expandable balloon; and a laser source couplable to the optical fiber of said device.

10. The apparatus of claim 9, further comprising one or more of the following components:

a suction member, connectable to said at least one suction pipe of the tubular suction member;

a washing liquid feed member, connectable to said at least one washing liquid feed pipe of the tubular suction member;

an expansion circuit adapted to feed an expansion fluid into the expandable balloon.

11. The apparatus of claim 10, wherein the expansion circuit is adapted to circulate the expansion fluid in the expandable balloon.

* * * * *